United States Patent
Cirjak et al.

Patent Number: 6,043,185
Date of Patent: Mar. 28, 2000

[54] GALLIUM PROMOTED MOLYBDENUM VANADIUM-ANTIMONY-OXIDE BASED CATALYST FOR SELECTIVE PARAFFIN AMMOXIDATION

[75] Inventors: Larry M. Cirjak, Burton Township; Anne Venturelli, North Royalton, both of Ohio; Timothy J. Cassidy, Buxton, United Kingdom; Marc A. Pepera, Northfield Center Township; Tama L. Drenski, Twinsburg, both of Ohio

[73] Assignee: The Standard Oil Company, Chicago, Ill.

[21] Appl. No.: 09/285,384

[22] Filed: Apr. 2, 1999

[51] Int. Cl.[7] .......................... B01J 23/00; C07C 253/00
[52] U.S. Cl. .................... 502/311; 502/312; 558/321; 558/323; 558/325
[58] Field of Search .................. 558/321, 323, 558/325; 502/311, 312

[56] References Cited

FOREIGN PATENT DOCUMENTS 19835247  2/1999  Germany .

*Primary Examiner*—Johann Richter
*Assistant Examiner*—Joseph Murray
*Attorney, Agent, or Firm*—David P. Yusko; Wallace L. Oliver

[57] ABSTRACT

A catalyst useful in the manufacture of acrylonitrile or methacrylonitrile by the catalytic reaction in the vapor phase of a paraffin selected from propane and isobutane with molecular oxygen and ammonia by catalytic contact of the reactants in a reaction zone with a catalyst, the feed composition having a mole ratio of the paraffin to ammonia in the range of about 1.0 to 10 and a mole ratio of paraffin to oxygen in the range of about 1.0 to 10, wherein said catalyst has the elements in the proportions indicated by the empirical formula:

$$MO_a V_b Sb_c Ga_d X_e O_x$$

where

X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal, and an alkaline earth metal, preferably Nb, Ce, Fe, Ge, Sn, In, As, Se, and B, especially preferred being Nb, a equals 1, b equals 0.0 to 0.99, preferably 0.1 to 0.5, c equals 0.01 to 0.9, preferably 0.05 to 0.5, d equals 0.01 to 0.5, preferably 0.01 to 0.4, e equals 0.0 to 1.0, preferably 0.0 to 0.9, x is determined by the oxidation state of the cations present.

18 Claims, No Drawings

GALLIUM PROMOTED MOLYBDENUM VANADIUM-ANTIMONY-OXIDE BASED CATALYST FOR SELECTIVE PARAFFIN AMMOXIDATION

BACKGROUND OF THE INVENTION

1. Field of the Invention

This invention relates to an improved catalyst for the ammoxidation of propane and isobutane to its corresponding α,β-unsaturated mononitriles (acrylonitrile and methacrylonitrile). Another aspect of the present invention is directed to the process in which propane and isobutane are reacted along with ammonia and oxygen in the presence of the catalyst to produce acrylonitrile and methacrylonitrile. The catalyst of the present invention may be utilized in a single pass or recycle process.

Nitriles, such as acrylonitrile and methacrylonitrile, have been industrially produced as important intermediates in the preparation of fibers, synthetic resins, synthetic rubbers and the like. The commercially dominant method for their production requires the ammoxidation of propylene or isobutylene in the presence of ammonia and oxygen at a high temperature in the gas phase in the presence of an ammoxidation catalyst.

However, in view of the price differential between propane and propylene, or the price difference between isobutane and isobutene, recent attention has been drawn to the development of a method and catalyst for the production of acrylonitrile or methacrylonitrile by an ammoxidation reaction wherein the lower alkane such as propane or isobutane is used as a starting material and such lower alkane is catalytically reacted with ammonia and an oxygen-containing gas in the presence of an ammoxidation catalyst.

Earlier attempts to develop an efficient process for the ammoxidation of propane to acrylonitrile produced either insufficient yields or processes that necessitated adding halogen promoters to the feed. The latter procedure would require not only reactors made of special corrosion resistant materials, but also a quantitative recovery or separation and removal of the promoter. This added cost eliminated the advantages of the propane/propylene price differential.

Recent published patent publications such as EPO 0767164-A1 and patents such as U.S. Pat. Nos. 5,231,214, 5,472,925: 5,422,328: 5,049,692 and 5,008,427 have been directed to ammoxidation catalyst systems which are directed to solving the problems of previous attempts at propane ammoxidation using specific catalysts. In particular, U.S. Pat. No. 5,008,427 assigned to the assignee of the present invention is specifically directed to a vanadium-antimony promoted catalyst for propane ammoxidation wherein the catalyst is calcined at temperatures of 780° C. or higher. The catalyst of the present invention and the ammoxidation procedure disclosed herein is directed to an improvement in process and catalyst disclosed in EPO 0767164-A1, the '214 and the '427 patents.

SUMMARY OF THE INVENTION

It is an object of the present invention to provide an improved catalyst for the ammoxidation of paraffins to their corresponding a, unsaturated mononitriles.

It is a further object of the present invention to provide an improved catalytic ammoxidation process for making unsaturated mononitriles from their corresponding lower paraffins.

It is a still further object of the present invention to provide a process for making a promoted mixed metal oxide catalyst useful in the ammoxidation of a paraffin to its α,β corresponding unsaturated mononitrile.

It is another object of the present invention to provide an improved catalyst for use in the ammoxidation of propane or isobutane to acrylonitrile or methacrylonitrile.

Other objects as well as aspects, features and advantages of the present invention will become apparent from the study of the accompanying disclosure and the claims.

To achieve the foregoing objects and advantages the catalyst of the present invention comprises a promoted $MoVSbGaO_x$ mixed metal oxide catalyst for use in producing an α,β-unsaturated mononitrile, e.g. acrylonitrile or methacrylonitrile, from a corresponding paraffin, e.g. propane or isobutane, characterized by the empirical formula set forth below:

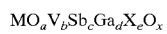

$$Mo_aV_bSb_cGa_dX_eO_x$$

where

X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal, and an alkaline earth metal, preferably Nb, Ce, Fe, Ge, Sn, In, As, Se, and B, especially preferred being Nb, a equals 1, b equals 0.0 to 0.99, preferably 0.1 to 0.5, especially preferred being 0.15 to 0.45, c equals 0.01 to 0.9, preferably 0.05 to 0.5, especially preferred being 0.05 to 0.45, d equals 0.01 to 0.5, preferably 0.01 to 0.4, especially preferred being 0.01 to 0.35, e equals 0.0 to 1.0, preferably 0.0 to 0.9, especially preferred being 0.0 to 0.85, x is determined by the oxidation state of the cations present.

In a preferred embodiment of the present invention the catalyst is substantially free of Te, especially preferred is a catalyst completely free of Te. For purposes of the present invention the term substantially free of Te means a catalyst containing less than 0.01 Te.

A further aspect of the present invention is directed to the process of manufacturing acrylonitrile and/or methacrylonitrile comprising introducing a hydrocarbon selected from the group consisting of propane and isobutane, ammonia, and oxygen into a reaction zone containing a catalyst comprising a promoted $MoVSbGaO_x$ mixed metal oxide wherein the catalyst is characterized by the following empirical formula:

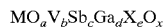

$$Mo_aV_bSb_cGa_dX_eO_x$$

where

X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal, and an alkaline earth metal, preferably Nb, Ce, Fe, Ge, Sn, In, As, Se, and B, especially preferred being Nb, a equals 1, b equals 0.0 to 0.99, preferably 0.1 to 0.5, especially preferred being 0.15 to 0.45, c equals 0.01 to 0.9, preferably 0.05 to 0.5, especially preferred being 0.05 to 0.45, d equals 0.01 to 0.5, preferably 0.01 to 0.4, especially preferred being 0.01 to 0.35, e equals 0.0 to 1.0, preferably 0.0 to 0.9, especially preferred being 0.0 to 0.85, x is determined by the oxidation state of the cations present.

DETAILED DESCRIPTION OF THE INVENTION

According to one aspect of the invention there is provided a process for making an α,β-unsaturated mononitrile, e.g. acrylonitrile or methacrylonitrile by the catalytic reaction in the vapor phase of a paraffin, e.g. propane and isobutane, oxygen (preferably introduced via an oxygen containing gas, e.g. air) and ammonia comprising contacting the paraffin, ammonia and oxygen in a reaction zone with a catalyst, the feed composition having a mole ratio of the paraffin to ammonia in the range of about 1.0 to 10, preferably 2 to 4, and a mole ratio of paraffin to oxygen in the range of about 1.0 to 10, preferably 1 to 3, wherein said catalyst has the elements in the proportions indicated by the empirical formula:

$$Mo_aV_bSb_cGa_dX_eO_x$$

where

X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal, and an alkaline earth metal, preferably Nb, Ce, Fe, Ge, Sn, In, As, Se, and B, especially preferred being Nb, a equals 1, b equals 0.0 to 0.99, preferably 0.1 to 0.5, especially preferred being 0.15 to 0.45, c equals 0.01 to 0.9, preferably 0.05 to 0.5, especially preferred being 0.05 to 0.45, d equals 0.01 to 0.5, preferably 0.01 to 0.4, especially preferred being 0.01 to 0.35, e equals 0.0 to 1.0, preferably 0.0 to 0.9, especially preferred being 0.0 to 0.85, x is determined by the oxidation state of the cations present.

Another aspect of the present invention is directed to the manufacture of the catalyst comprising preparing the catalyst of the present invention in two stages. In the first stage, a catalyst precursor is calcined in an oxidizing environment (e.g. air) at a temperature of between 275° C. to 400° C., preferably between about 275° C. to 325° C. for about 15 minutes to 8 hours, preferably between about 1 to 3 hours. In the second stage, the catalyst is calcined in a non-oxidizing environment such as argon, nitrogen or helium at a temperature of between 500° C. to 700° C., preferably between 550° C. to 650° C. for about 15 minutes to 8 hours, preferably between about 1 to 3 hours. Optionally, a reducing gas such as ammonia or hydrogen may be added during the second stage calcination.

Although any type of furnace may be utilized during the calcination of the catalyst, it is preferred to conduct the calcination under a flow of the designated gas environment. Therefore, it is advantageous to conduct the calcination in a moving bed such as a rotary calciner or a fluid bed calciner with continuous flow of the above described gas mixtures through the bed of solid catalyst particles.

The starting materials suitable for the manufacture of the catalyst of the present invention are metal oxides or metal salts such as metal halides or metal nitrates. For example, ammonium heptamolybdate may be utilized for the source of the molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of the vanadium in the catalyst. However, compounds such as $V_2O_5$, $V_2O_3$, $VOCl_3$, $VCl_4$, $VO(OC_2H_5)_3$, vanadium acetylacetonate, vanadyl acetylacetonate may also be utilized instead of ammonium metavanadate. The antimony source may include $Sb_2O_4$, $Sb_2O_5$, $SbOCl_3$, $SbCl_5$, $Sb(OC_2H_5)_3$ as well as the more conventional $Sb_2O_3$. The niobium source may include ammonium niobium oxalate, $Nb_2O_5$, $NbCl_5$, niobic acid or $Nb(OC_2H_5)_5$ as well as the more conventional niobium oxalate. The typical gallium source such as $Ga_2O_3$ may be substituted by $Ga_2O$, $GaCl_3$, $GaCl_2$, gallium acetylacetonate, or $Ga(NO_3)_3$. Sources for Ce as well as other X elements include metal nitrates, metal halides and metal oxides.

Typical reaction conditions for the ammoxidation of propane or isobutane to acrylonitrile and methacrylonitrile may be utilized in the practice of the present invention. The process may be practiced in single pass or recycle mode. General conditions for the process of the present invention are as follows: reaction temperature range can vary from 350° to 700° C., but is usually between 400° to 475° C.; average contact time can often be from 0.01 to 10 seconds but is usually between 0.02 to 10 seconds and more, preferably between 0.1 to 5 seconds; pressure in the reaction zone usually ranges from 0 to 75 psig, but is preferably no more than 50 psig. In a single pass process it is preferred that oxygen be supplied from an oxygen containing gas such as air. The single pass process may also be practiced with oxygen addition. In the practice of the recycle mode, oxygen gas by itself is the preferred source to avoid build up of inert gases in the reaction zone. For more details as to the typical conditions utilized in ammoxidation reactions see U.S. Pat. No. 5,008,427 herein incorporated by reference.

Of course, in the ammoxidation reaction of the present invention it is important that the hydrocarbon and oxygen concentrations in the feed gases be maintained at the appropriate levels to minimize or avoid entering a flammable regime either within the reaction zone or especially at the outlet of the reactor zone. Generally, it is preferred that the outlet oxygen levels be low to both minimize after-burning and, particularly, in the recycle mode of operation to minimize the amount of oxygen in the recycled gaseous effluent stream. In addition, operation of the reaction at a low temperature (below 475° C.) is extremely attractive because after-burning becomes less of a problem which enables the attainment of higher selectivity to the desired products. The catalyst of the present invention operates more efficiently at the lower temperature range set forth above, significantly reducing the formation of HCN and increasing selectivity to acylonitrile and acetonitrile.

In the recycle process of the present invention, the reaction takes place in a fluid bed reactor which is equipped for recycle of the unreacted propane and generated propylene back into the fluid bed reactor. It is anticipated that a substantial portion of the recycled propylene would be converted to acrylonitrile.

Another aspect of the present invention is directed to a catalyst useful in the ammoxidation of propane to acryloni trile comprising a promoted $MoVSbGaO_x$ mixed metal oxide catalyst characterized by the elements and the proportions indicated by the empirical formula set forth below:

$$Mo_aV_bSb_cGa_dX_eO_x$$

where

X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal, and an alkaline earth metal, preferably Nb, Ce, Fe, Ge, Sn, In, As, Se, and B, especially preferred being Nb, a equals 1, b equals 0.0 to 0.99, preferably 0.1 to 0.5, especially preferred being 0.15 to 0.45, c equals 0.01 to 0.9, preferably 0.05 to 0.5, especially preferred being 0.05 to 0.45, d equals 0.01 to 0.5, preferably 0.01 to 0.4, especially preferred being 0.01 to 0.35, e equals 0.0 to 1.0, preferably 0.0 to 0.9, especially preferred being 0.0 to 0.85, x is determined by the oxidation state of the cations present.

It is envisioned that the catalyst of the present invention can be utilized in either an unsupported or supported form. If the catalyst is supported conventional supports such as silica, alumina, zirconia and mixtures thereof may be utilized.

The examples set forth below are for illustrative purposes only and should not be considered as limiting the scope of the invention.

EXAMPLES

Comparative Example 1

A catalyst of nominal composition $Mo_{1.0}V_{0.3}Sb_{0.15}Nb_{0.05}Ce_{0.03}O_x$ was prepared in the following manner. 17.13 g of $NH_4VO_3$ was dissolved in 350 mL of water at approximately 95° C. to give a yellow solution. 10.57 g of $Sb_2O_3$ was added and heated for 5 hours at 95° C. giving a dark gray slurry. After 5 hours, water was removed by evaporation until 187 g of material remained. 86.17 g of $(NH_4)_6Mo_7O_{24}$ was added to give a purple slurry. After stirring for 5 minutes, the mixture was cooled to room temperature with an ice bath. 15.44 g of niobium oxalate (21% $Nb_2O_5$) was dissolved in 80 mL of water and was added to the cooled mixture, followed by 3.05 g of $Ce(OH)_4$. The mixture was stirred vigorously for 30 minutes and then spray dried. 40 g of the material obtained was calcined for 2 hours under a flow of air at 300° C. followed by a 615° C. fluidized bed calcination under a flow of nitrogen for 2 hours.

Example 1

A catalyst of nominal composition $Mo_{1.0}V_{0.3}Sb_{0.15}Nb_{0.05}Ga_{0.03}O_x$ was prepared in the following manner. 17.33 g of $NH_4VO_3$ was dissolved in 350 mL of water at approximately 95° C. to give a yellow solution. 10.79 g of $Sb_2O_3$ was added and heated for 5 hours at 95° C. giving a dark gray slurry. After 5 hours, water was removed by evaporation until 187 g of material remained. 86.17 g of $(NH_4)_6Mo_7O_{24}$ was added to give a purple slurry. After stirring for 5 minutes, the mixture was cooled to room temperature with an ice bath. 15.62 g of niobium oxalate (21% $Nb_2O_5$) was dissolved in 80 mL of water and was added to the cooled mixture, followed by 1.39 g of $Ga_2O_3$. The mixture was stirred vigorously for 30 minutes and then spray dried. 40 g of the material obtained was calcined in an upright tubular reactor at 300° C. with 250 cc/min of air followed by 615° C. under a flow of nitrogen.

The two catalysts were tested with a feed ratio of propane/$NH_3$/$O_2$/$N_2$/$H_2O$ of 1.0/1.4/3.3/12.3/4.0 in a 5cc fixed bed reactor at 460° C. at atmospheric pressure. The results are set forth below in Table I.

TABLE 1

| Ex | wwh $hr^{-1}$ | % $C_3°$ Conv | % Sel AN | % Sel HCN | % Sel $C_3^=$ | % Sel Acr Acid | % Sel Aceto | % Sel CO | % Sel $CO_2$ | % Yld AN |
|---|---|---|---|---|---|---|---|---|---|---|
| 1 (Comp) | .107 | 71.0 | 50.7 | 6.0 | 1.0 | 1.5 | 6.8 | 20.5 | 13.6 | 36.0 |
| 1 | .080 | 81.2 | 45.8 | 4.3 | 1.6 | 3.4 | 4.7 | 20.3 | 19.9 | 37.2 |

AN = acrylonitrile;
$C_3^=$ = propylene;
Acr Acid = acrylic acid;
Aceto = acetonitrile;
$C_3°$ = propane;
wwh = weight of hydrocarbon feed per hour/weight of catalyst in the reactor

Examples 2 to 6

A catalyst of nominal composition $Mo_{1.0}V_{0.3}Sb_{0.15}Nb_{0.05}Ga_{0.03}O_x$ was prepared in a similar manner as in Example 1 except that the niobium oxalate solution was stirred overnight and the gallium oxide was ground into a fine powder and stirred in warm water for several hours prior to use.

The catalysts were tested under varied feed ratios of propane/$NH_3$/$O_2$/$N_2$/$H_2O$. The feed mix employed in Examples 1 and 2 above is typical of what one would expect if air were employed as the source for use in a single pass mode. In Examples 5 and 6 the feed mix is more appropriate for use in a recycle mode where oxygen is fed directly into the reactor. The results are set forth below in Table II. In Example 2, the feed ratio of propane/$NH_3$/$O_2$/$N_2$/$H_2O$ was 1.0/1.2/3.3/12.3/4.0. Examples 3 and 4 used a feed ratio of 2.0/1.1/2.1/12.0/2.0 intermediate between a single pass and recycle mode. Examples 5 and 6 had a feed ratio of 3.0/1.0/1.8/2.0/0.0 and 3.0/0.9/1.9/2.0/0.0, respectively (Recycle Conditions). The pressure for Examples 2 to 5 was 0 psig while the pressure for example 6 was 15 psig.

Examples 7 to 10

A catalyst of nominal composition $Mo_{0.1}V_{0.3}Sb_{0.15}Nb_{0.05}Ga_{0.06}O_x$ was prepared in a similar manner to the catalyst employed in Example 1 except that the final slurry was homogenized briefly prior to spray drying. However, in examples 7 and 8 the catalyst was calcined at approximately 615° C. while the calcination temperature in Examples 9 and 10 was about 625° C.

Similar to the previous examples, the catalysts of Examples 7–10 were tested under varied feed ratios of propane/$NH_3$/$O_2$/$N_2$/$H_2O$. Examples 7 and 9 were tested under the following single pass conditions: the feed ratio of propane/$NH_3$/$O_2$/$N_2$/$H_2O$ was 1.0/1.2/3.1/11.9/2.0 at 0 psig. Examples 8 and 10 were tested under the following recycle conditions: the feed ratio of propane/$NH_3$/$O_2$/$N_2$/$H_2O$ was 3.0/0.9/1.9/2.0/0.0 at 15 psig.

TABLE 2

| Ex | Temp °C. | wwh hr$^{-1}$ | $NH_3$ ratio | $C_3°$ Conv | % Sel AN | % Sel HCN | % Sel Aceto | % Sel Acr Acid | % Sel $C_3^=$ | % Sel $CO_x$ | % Yld AN |
|---|---|---|---|---|---|---|---|---|---|---|---|
| 2 | 420 | 0.070 | 1.2 | 83.1 | 53.3 | 5.2 | 5.2 | 0.7 | 1.3 | 34.2 | 44.2 |
| 3 | 410 | 0.150 | 1.1 | 41.6 | 60.3 | 3.5 | 7.9 | 0.4 | 7.9 | 19.9 | 25.1 |
| 4 | 410 | 0.290 | 1.1 | 38.4 | 54.6 | 5.5 | 7.9 | 0.8 | 9.2 | 22.0 | 21.0 |
| 5 | 410 | 0.450 | 1.0 | 25.6 | 54.8 | 3.2 | 8.5 | 0.4 | 17.1 | 15.9 | 14.0 |
| 6 | 410 | 0.910 | 0.9 | 25.8 | 47.3 | 2.4 | 8.5 | 2.3 | 19.6 | 20.0 | 12.2 |
| 7 | 410 | 0.078 | 1.2 | 85.9 | 47.0 | 6.1 | 2.6 | 0.8 | 0.0 | 43.6 | 40.4 |
| 8 | 410 | 0.973 | 0.9 | 26.8 | 47.1 | 2.2 | 9.5 | 1.5 | 20.2 | 19.2 | 12.6 |
| 9 | 410 | 0.086 | 1.2 | 81.2 | 42.8 | 6.4 | 4.7 | 0.7 | 0.0 | 45.4 | 34.8 |
| 10 | 410 | 1.068 | 0.9 | 27.3 | 49.8 | 2.1 | 8.1 | 3.1 | 19.9 | 16.8 | 13.6 |

While the invention has been described in conjunction with the specific embodiments set forth above, it is evident that many alternatives, modifications and variations will be apparent to those skilled in the art in light of the foregoing description. Accordingly, it is intended to embrace all such alterations, modifications and variations as fall within the spirit and broad scope of the appended claims.

What we claim as our invention is:

1. A process for making acrylonitrile or methacrylonitrile by the catalytic reaction in the vapor phase of a paraffin selected from propane and isobutane with oxygen and ammonia by catalytic contact of the reactants in a reaction zone with a catalyst, the feed composition having a mole ratio of the paraffin to ammonia in the range of about 1.0 to 10 and a mole ratio of paraffin to oxygen in the range of about 1.0 to 10, wherein said catalyst is represented by the following empirical formula:

$$Mo_aV_bSb_cGa_dX_eO_x$$

where

X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal, and an alkaline earth metal, a equals 1, b equals 0.0 to 0.99, c equals 0.01 to 0.9, d equals 0.01 to 0.5, e equals 0.0 to 1.0, x is determined by the oxidation state of the cations present, and wherein the catalyst is free of Te.

2. The process of claim 1 wherein X is selected to be Nb.
3. The process of claim 1 wherein b is between 0.1 to 0.5.
4. The process of claim 1 wherein c is between 0.05 to 0.5.
5. The process of claim 1 wherein d is between 0.01 to 0.4.
6. The process of claim 1 wherein e is between 0.0 to 0.9.
7. The process of claim 1 wherein the reaction takes place in a fluid bed reactor.
8. The process of claim 7 wherein any unreacted propane or isobutane is recycled into the fluid bed reactor.
9. The process of claim 1 wherein b is greater than zero.
10. The process of claim 9 wherein X is selected to be Nb.
11. The process of claim 10 wherein b is between 0.1 to 0.5.
12. The process of claim 11 wherein c is between 0.05 to 0.5.
13. The process of claim 12 wherein d is between 0.01 to 0.4.
14. The process of claim 13 wherein e is between 0.0 to 0.9.
15. A catalyst useful in the ammoxidation of propane and isobutane to acrylonitrile and methacrylonitrile comprising a promoted mixed metal oxide $Mo_aV_bSb_cGa_dX_eO_x$ catalyst represented by the following empirical formula:

$$Mo_aV_bSb_cGa_dX_eO_x$$

where

X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal, and an alkaline earth metal, a equals 1, b equals 0.0 to 0.99, c equals 0.01 to 0.9, d equals 0.01 to 0.5, e equals 0.0 to 1.0, x is determined by the oxidation state of the cations present, and wherein the catalyst is free of Te.

16. The catalyst of claim 15 wherein b is greater than zero.
17. The catalyst of claim 16 wherein X is selected to be Nb.
18. A process for the manufacture of a catalyst comprising the elements set forth in the following empirical formula $$Mo_aV_bSb_cGa_dX_eO_x$$

where

X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal, and an alkaline earth metal, a equals 1, b equals 0.0 to 0.99, c equals 0.01 to 0.9, d equals 0.01 to 0.5, e equals 0.0 to 1.0, x is determined by the oxidation state of the cations present, wherein the process comprises forming an aqueous slurry containing at least a molybdenum compound, gallium compound, antimony compound and optionally a vanadium and X element compound, drying the aqueous mixture to remove the water, calcining the dried mixture in an oxidizing environment at a temperature of between 275° C. to 400° C. to form a catalyst precursor, and calcining the catalyst precursor in a non-oxidizing environment at a temperature of between 500° C. to 700° C. to form the finished catalyst.

* * * * *

UNITED STATES PATENT AND TRADEMARK OFFICE
CERTIFICATE OF CORRECTION

PATENT NO. : 6,043,185
DATED : March 28, 2000
INVENTOR(S) : Larry M. Cirjak, et. al.

It is certified that error appears in the above-identified patent and that said Letters Patent is hereby corrected as shown below:

| Col. | Line | |
|---|---|---|
| 1 | 61 | "corresponding a, unsaturated" <br><br> should read: <br> "corresponding $\alpha,\beta$ unsaturated" |
| 7 | 47 | "one or more of As, Te, Se, Nb," <br><br> should read: <br> "one or more of As, Se, Nb," |
| 8 | 33 | "one or more of As, Te, Se, Nb," <br><br> should read: <br> "one or more of As, Se, Nb," |

Signed and Sealed this

Sixth Day of February, 2001

Attest:

Q. TODD DICKINSON

*Attesting Officer*     *Director of Patents and Trademarks*